United States Patent [19]
Shafer

[11] Patent Number: 5,660,546
[45] Date of Patent: Aug. 26, 1997

[54] DENTURE CLEANING KIT AND PROCESS

[76] Inventor: Joseph G. Shafer, P.O. Box 447, Solana Beach, Calif. 92075

[21] Appl. No.: 531,725

[22] Filed: Sep. 21, 1995

Related U.S. Application Data

[63] Continuation-in-part of Ser. No. 373,037, Jan. 17, 1995, abandoned.

[51] Int. Cl.⁶ .................................................. A61C 15/00
[52] U.S. Cl. ........................... 433/216; 433/166; 132/308; 206/581
[58] Field of Search ..................... 433/216, 166, 433/125, 142; 132/308, 309; 15/28, 29; 206/572, 581, 369, 63.5, 368

[56] References Cited

U.S. PATENT DOCUMENTS

| | | | |
|---|---|---|---|
| 1,993,763 | 3/1935 | Touchstone | 433/166 |
| 3,718,973 | 3/1973 | Slater et al. | 433/84 |
| 3,902,279 | 9/1975 | Lookadoo | 433/166 |
| 3,939,599 | 2/1976 | Henry et al. | 433/125 |
| 4,031,671 | 6/1977 | Frosz | 51/263 |
| 4,913,282 | 4/1990 | Didier | 206/581 |
| 4,984,323 | 1/1991 | Digby | 15/28 |

*Primary Examiner*—Cary E. O'Connor
*Attorney, Agent, or Firm*—John R. Ross

[57] ABSTRACT

A home denture cleaning kit for cleaning dentures. The kit includes at least a one year's supply of dental pumice, at least a one year supply of tin oxide and an electric driven rotating brush. In a preferred embodiment the bristles of the brush are at least ½ inch long and no longer than about 1 ¼ inch and are aligned generally parallel to the axis of rotation of the brush. Dentures are cleaned by mixing about one gram of pumice with an equal quantity of water to form a paste which is applied to the dentures. The rotating brush is then used to brush the pumice-water paste against the denture material to remove film and surface stains such as those due to coffee and tea. After the teeth are cleaned, approximately ⅛ gram of tin oxide powder is mixed with an equal quantity of water and applied to the teeth portion of the dentures. The rotating buffing wheel is then used to buff the tin-oxide paste against the dentures in order to produce a shine on the dentures.

4 Claims, 3 Drawing Sheets

DENTURE CLEANING KIT AND PROCESS

This is a continuation-in-part application of Ser. No. 08/373,037 filed Jan. 17, 1995, now abandoned.

This invention relates to denture cleaning devices and processes and in particular to processes and denture cleaning devices for home use.

BACKGROUND OF THE INVENTION

A substantial percentage of the population of the world wear removable dentures. These dentures should be cleaned at least once each day. Usually they are removed for cleaning. Popular cleaning methods include solutions sold under the trade names of Efferdent™ and Polydent™ in which dentures are soaked to remove stains bacteria and other foreign matter. Dentures are also cleaned with tooth brushes using various commercially available toothpastes.

Pumice is a rock froth, formed by the extreme puffing up of liquid lava by expanding gasses liberated from solution in the lava prior to and during solidification. A fine powder made from ground up pumice is commonly used by dental laboratories for cleaning dentures. This fine powder is called "dental pumice". One well known supplier of dental pumice is the Sybron Dental Products Division of Kerr Co., Emeryville, Calif. This product is advertised to be made up of the following elements:

| | |
|---|---|
| Ca | 0.776% |
| Mg | 0.716% |
| Na | 1.599% |
| K | 1.752% |
| Al(203) | 14.262% |
| SiO2 | 69.610% |

Tin oxide, also called stannic oxide, is a white powder used to create ceramic glazes. It is known that tin oxide can produce a shine on dentures when the dentures are rubbed with the powder.

What is needed is a home denture cleaning kit which will permit owners of dentures to clean their dentures as well and as efficiently as dental laboratories.

SUMMARY OF THE INVENTION

The present invention utilizes some of the well established techniques of denture laboratories to provide a home denture cleaning kit for cleaning dentures. The kit includes at least a one year's supply of dental pumice, at least a one year supply of tin oxide and an electric driven rotating brush. In a preferred embodiment the bristles of the brush are at least ½ inch long and no longer than about 1 ¼ inch and are aligned generally parallel to the axis of rotation of the brush. Dentures are cleaned by mixing about one gram of pumice with an equal quantity of water to form a paste which is applied to the dentures. The rotating brush is then used to brush the pumice-water paste against the denture material to remove film and surface stains such as those due to coffee and tea. After the teeth are cleaned, approximately ⅛ gram of tin oxide powder is mixed with an equal quantity of water and applied to the teeth portion of the dentures. The rotating buffing wheel is then used to buff the tin-oxide paste against the dentures in order to produce a shine on the dentures.

BRIEF DESCRIPTION OF THE DRAWINGS

FIG. 5 shows the elements of a preferred kit for cleaning dentures.

DETAILED DESCRIPTION OF PREFERRED EMBODIMENTS

A preferred embodiment of the present invention can be described by reference to the drawings.

Figure 1:
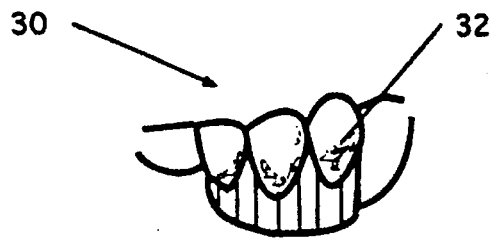
FIGS. 1 through 5 demonstrate a portion of a preferred process for cleaning dentures according the present invention.
Figure 2:
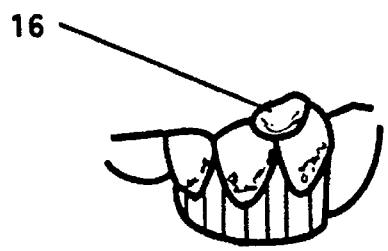
Figure 3:
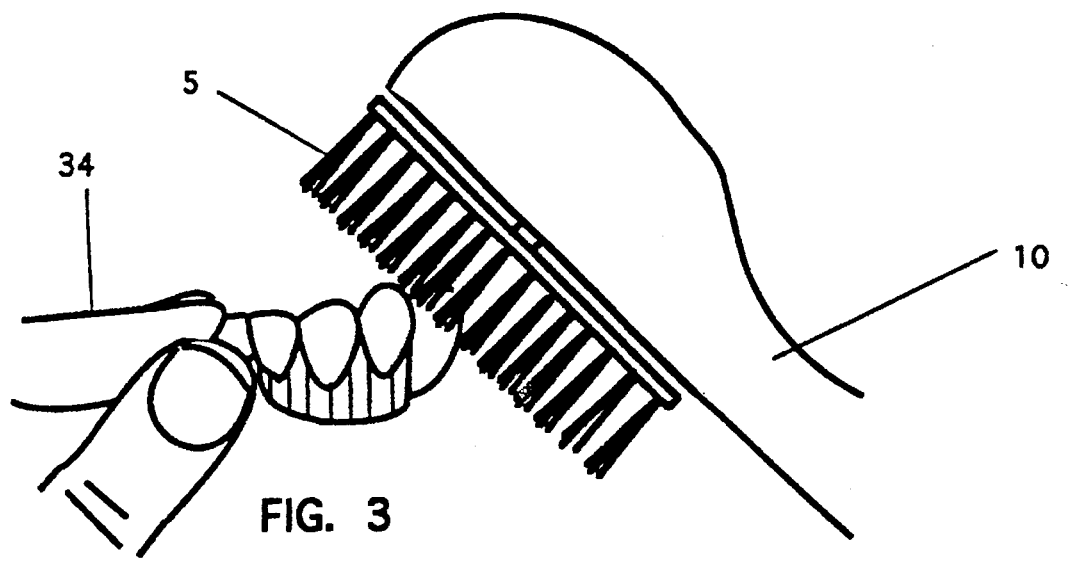
Figure 4:
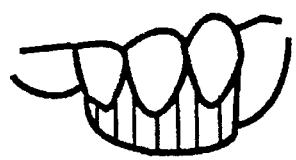
Figure 5:
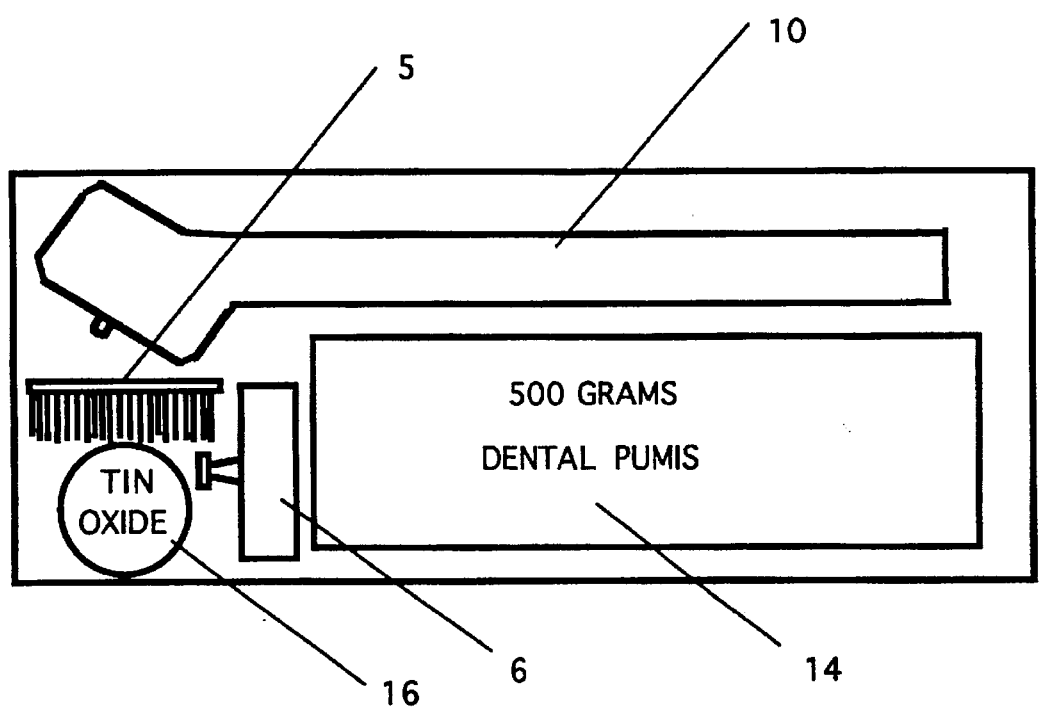
Figure 6:
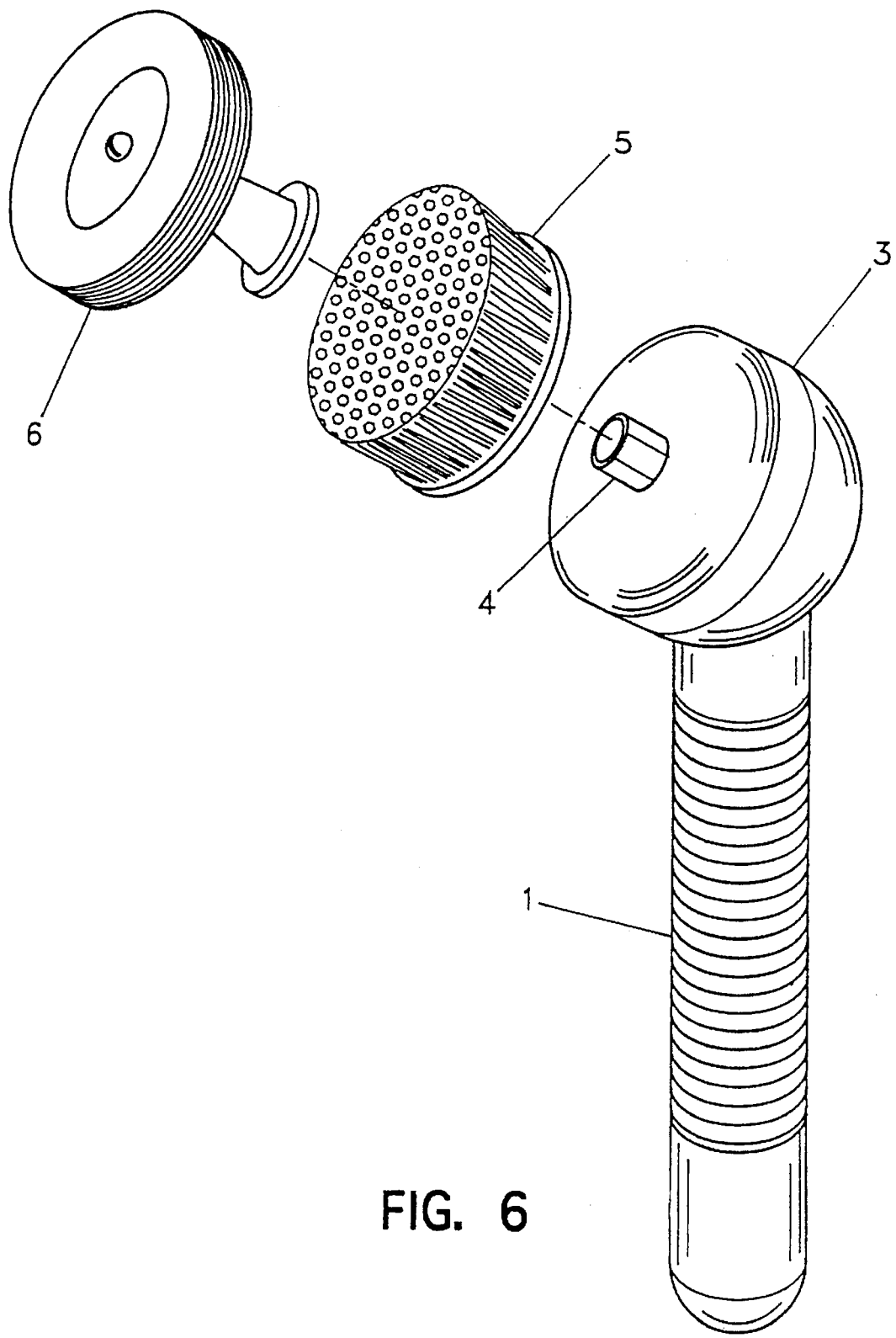
FIG. 6 is a drawing of a preferred brush for use in accordance with the present invention.

The elements of a preferred home denture cleaning kit are shown in FIG. 5. These are a battery powered electric brush driver 10, a brush 5, a buffing wheel 6, a package containing 500 grams of dental pumice 14, and a package containing 80 grams of tin oxide 16. FIG. 6 shows an assembly drawing of electric brush driver 10, brush 5 and buffing wheel 6. FIG. 1 shows a stained denture 30 with stains at 32. FIG. 2 shows a one gram blob of a pumice-water paste 16 applied to denture 30. FIG. 3 shows the brush 5 cleaning denture 30 while being held by fingers 34. After all stains have been removed by brushing with the pumice-water paste, the dentures and the brush are rinsed with water. Next a small blob about 0.1 gram of tin oxide paste is smeared on the denture and buffing wheel 6 is used to give the dentures a bright shine leaving the dentures clean and shiny as depicted in FIG. 4.

The pumice paste preferably is made by mixing one part pumice with one part water. The tin oxide paste is make by mixing two parts tin oxide with one part water.

The brush driver has a length of about 9¾ inches, The driver includes a battery holder part 1 and a motor housing 3. Protruding about ½ inch from the motor housing is protrusion 4 which is plastic and an extension of the shaft of the motor (not shown) of the driver. Protrusion 4 is cut twice ⅜ inch deep at right angles to the centerline of the axle so that the protrusion is made up of four flexible plastic extensions. The bottom of protrusion 4 has a hexagonal cross section with opposite faces spaced apart by 5/16 inch. The outer dimension of the top of protrusion 4 is generally circular with a 5/16-inch diameter. Brush 5 contains 2 inch diameter bristle mounting plate 24 on which bristles 26 are mounted. A hexagonal cross section hole slightly larger in size and shape than the hexagonal portion of protrusion 4 extends through the center of bristle mounting plate 24. On the bristle side of bristle mounting plate the hexagonal hole is covered with a plate with a ¼ inch diameter circular hole. Thus, when protrusion 4 is pressed into hole of brush 5, the top of protrusion flexes and extends through the ¼ inch hole holding brush 12 in place. A pulling force of about ⅓ pound is sufficient to dislodge brush 12 from protrusion 4. Buffing wheel 6 contains a similar hole for attaching and removing buffing wheel 6 from driver 10.

With the quantities of pumice and tin oxide provided and the quantities specified to be used. Dentures could be cleaned and polished once per day for more than one year. Pumice and tin oxide is very inexpensive. The brush and the brush driver will cost about $20. Therefore, the entire package could sell for about $30. This is then an extremely economical package for denture cleaning. More economy can be realized by catching the used pumice during the cleaning process. This is a routine practice in denture laboratories. If in addition the teeth are polished with the tin oxide once per week, the materials in the kit should last many years, probably lifetime for many elderly denture wearers. Thus, a $30 purchase can provide clean dentures for a lifetime. This invention will also be a major time saver. Once the denture user learns how to use this kit, the process of cleaning and shining the dentures takes only a minute or two. This compares the alternative of hours of soaking dentures.

Although the description above contains many specificities, these should not be construed as limiting the scope of the invention but merely providing illustrations of some of the presently preferred embodiments of this invention. For example, many other electric brushes could be used so long as the flexibility of the bristles and the speed of the brush is similar to the example given. It is important to provide enough force with the bristles and the pumice to remove stains without any significant wear to the denture materials. The tin oxide could be applied with a soft cloth instead of the electric driver and buffing wheel. The quantities of the pumice and tin oxide could vary; however, an important element of this invention is that a very long term supply of these materials (at least a quantity sufficient for one-year of use) is provided with the kit.

Thus the scope of the invention should be determined by the appended claims and their legal equivalents, rather than by the examples given.

I claim:

1. A denture cleaning kit comprising:
   A) a hand held electric brush comprising:
      (1) a handle,
      (2) an electric motor encased in a housing and mounted at one end of said handle, said motor comprising a motor shaft defining a shaft axis,
      (3) a brush comprising:
         a) an attaching means for attaching said brush to said motor shaft,
         b) a plurality of bristles having lengths of at least ½ inch, the lengths of said bristles defining bristle directions said directions being generally parallel to said shaft axis when said brush is attached to said motor shaft,
   B) at least 500 grams of pumice powder and a pumice container means for containing said dental pumice,
   C) at least 80 grams of tin oxide powder and a tin oxide container means for containing said tin oxide.

2. A denture cleaning kit as in claim 1 wherein said pumice powder is dental pumice.

3. A process for keeping dentures clean and shiny for a period of one year comprising the steps of:
   A) cleaning said dentures substantially every day for said one year period with a cleaning process comprising the steps of:
      (1) placing a pumice and water paste on said dentures
      (2) brushing said dentures with an electric hand-held brush having flexible bristles at least ½ inch long,
      (3) rinsing said dentures with water.

4. A process as in claim 3 further comprising the step of shining said dentures at least once per month with a shining process comprising the steps of:
   (1) placing a tin oxide and water paste on said dentures,
   (2) brushing said dentures with an electric hand-held brush having flexible bristles at least ½ inch long,
   (3) rinsing said dentures with water.

* * * * *